(12) United States Patent
Kartoun et al.

(10) Patent No.: US 11,386,984 B2
(45) Date of Patent: Jul. 12, 2022

(54) NOTATION ASSISTANT SYSTEM FOR PROVIDING FEEDBACK ON A CLINICAL NARRATIVE NOTE

(71) Applicant: International Business Machines Corporation, Armonk, NY (US)

(72) Inventors: Uri Kartoun, Cambridge, MA (US); Kenney Ng, Arlington, MA (US); Tanya Rudakevych, Boston, MA (US); Charalambos Stavropoulos, Hastings-on-Hudson, NY (US); Francis Campion, Westwood, MA (US); Paul C. Tang, Los Altos, CA (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 646 days.

(21) Appl. No.: 16/375,416

(22) Filed: Apr. 4, 2019

(65) Prior Publication Data
US 2020/0321085 A1    Oct. 8, 2020

(51) Int. Cl.
*G16H 10/60* (2018.01)
*G06N 20/00* (2019.01)
(Continued)

(52) U.S. Cl.
CPC .......... *G16H 10/60* (2018.01); *G06F 40/169* (2020.01); *G06F 40/205* (2020.01); *G06N 20/00* (2019.01)

(58) Field of Classification Search
CPC ...... G16H 10/60; G06N 20/00; G06F 40/205; G06F 40/169
See application file for complete search history.

(56) References Cited

U.S. PATENT DOCUMENTS 7,783,620 B1 *  8/2010  Chevalier ......... G06F 16/24578
                                                707/706
8,612,261 B1    12/2013  Swanson et al.
(Continued)

OTHER PUBLICATIONS

Eixhauser A, Owens P. Reasons for being admitted to the hospital through the emergency department, 2003. HCUP Statistical Brief No. 2. Rockville, MD: Agency for Health Care Research and Quality, Feb. 2006.
(Continued)

*Primary Examiner* — John P Go
(74) *Attorney, Agent, or Firm* — Troutman Pepper Hamilton Sanders LLP

(57) ABSTRACT

A notation assistant system has a machine learning system, a notation processing system, a scoring system, and a suggestion system. The machine learning system trains a classifier for rating a factor related to a clinical narrative note that describes a patient's health status. The notation processing system processes a clinical narrative note and the scoring system determines a factor rating, such as a completion score or a clarity score. The scoring system provides the factor rating to an end-user device to display to a user. The notation assistant system is configured to perform a method as a user is entering a clinical narrative note to provide real-time feedback, such as the factor rating. The suggestion system is configured to provide suggestions for modifying the clinical narrative note to improve the rating factor. The notation assistant system applies to patient health conditions such as a health status of a patient's heart for a patient receiving care for congestive heart failure.

19 Claims, 8 Drawing Sheets

(51) Int. Cl.
*G06F 40/169* (2020.01)
*G06F 40/205* (2020.01)

(56) References Cited

U.S. PATENT DOCUMENTS

| | | | | |
|---|---|---|---|---|
| 2011/0301966 | A1* | 12/2011 | Kartoun | G16H 70/60 |
| | | | | 705/2 |
| 2013/0191161 | A1 | 7/2013 | Churchwell et al. | |
| 2013/0297347 | A1 | 11/2013 | Cardoza et al. | |
| 2014/0272832 | A1* | 9/2014 | Mitkov | G09B 7/00 |
| | | | | 434/219 |
| 2015/0324523 | A1* | 11/2015 | Parthasarathy | G16H 15/00 |
| | | | | 705/2 |
| 2016/0012187 | A1 | 1/2016 | Zasowski et al. | |
| 2018/0203978 | A1* | 7/2018 | Basu | G16H 50/70 |

OTHER PUBLICATIONS

Russo CA, Andrews RM. The national hospital bill: the most expensive conditions, by payer, 2004. HCUP Statistical Brief No. 13. Rockville, MD: Agency for Healthcare Research and Quality, Sep. 2006.

* cited by examiner

Patient A

*Progress note*

Signs and symptoms documentation
Completion: 47%
Ambiguity: 36%

This 83 year old woman with a history of congestive heart failure, and coronary artery disease risk factors of hypertension and post-menopausal state presents with substernal chest pain. On exam she was found to be in sinus tachycardia, with no JVD, but there are bibasilar rales and pedal edema, suggestive of some degree of congestive heart failure. There were EKG changes indicate an acute anterolateral myocardial infarction, and the labs shows elevation of CPK and troponin.

*FIG. 6*

Patient A

*Progress note*

Signs and symptoms documentation
Completion: 47%
Ambiguity: 36%

This 83 year old woman with a history of congestive heart failure, and coronary artery disease risk factors of hypertension and post-menopausal state presents with substernal chest pain. On exam she was found to be in sinus tachycardia, with no JVD, but there are bibasilar rales and pedal edema, suggestive of some degree of congestive heart failure. There were EKG changes indicate an acute anterolateral myocardial infarction, and the labs shows elevation of CPK and troponin.

700

Completion: 47%

Suggest:

Add Lab Test Information
Add Compensation Status
Add Pain Rating
Add Family History

Patient A

Progress note                                                                 800

Signs and symptoms documentation
Completion: 47%
Ambiguity: 36%

This 83 year old woman with a history of congestive heart failure, and coronary artery disease risk factors of hypertension and post-menopausal state presents with substernal chest pain. On exam she was found to be in sinus tachycardia, with no JVD, but there are bibasilar rales and pedal edema, suggestive of some degree of congestive heart failure. There were EKG changes indicate an acute anterolateral myocardial infarction, and the labs shows elevation of CPK and troponin.

805

**Ambiguous Phrasing
Consider Revising**

Select:
1.) Suggesting heart is decompensated
2.) Suggesting decompensation is more likely than not
3.) Suggesting heart is compensated
4.) Suggesting deleting phrase

NOTATION ASSISTANT SYSTEM FOR PROVIDING FEEDBACK ON A CLINICAL NARRATIVE NOTE

TECHNICAL FIELD

The present application relates to a notation assistant system and, more particularly, to a notation assistant system for providing feedback on a clinical narrative note.

BACKGROUND

Congestive heart failure (CHF) is a chronic condition occurring at the end-stage of life that affects millions of individuals every year. After pneumonia, CHF is the second most common cause of hospital admission. The financial burdens associated with CHF care are immense; in 2004, the 1.1 million U.S. admissions for CHF amounted to nearly $29 billion in hospital charges.

In addition to frequent admissions that characterize CHF patients, such patients often meet their primary care physician in the outpatient setting. In such outpatient encounters (also called "office visits") the physician attempts to assess the level of severity of the disease. The physician (or other clinician, such as a nurse) documents the status of the patient by recording information such as visible signs and observations, symptoms and conditions, test results, measurements, and the like. Often, this information is documented in the patient's chart via a clinical narrative note—a typed entry by the physician containing information obtained during the visit. This note becomes a crucial part of the patient's medical record, as it is a snapshot of the patient's health at a point in time.

For CHF patients the clinical narrative note is an effective tool for recording the overall health status of a patient's heart, such as whether the heart failure is compensated (desirable status) or decompensated (severe status), as this is often up to the physician's judgment based on all relevant factors. Clearly and completely documenting the relevant factors ensures a clear medical record and assists in determining the patient's heart's health status. Furthermore, a clear and complete record enables the physician to provide effective advice for maintaining the patient's heart failure in a compensated state.

Given the importance of the clinical narrative note, especially for CHF patients, it is problematic when the note does not include sufficient information to enable one to accurately determine the patient's health status from the record. Often a note contains comprehensive details on the patient's heart; however, it may still not be straightforward for a reader thereof to determine if the patient's heart's failure is in a compensated or a decompensated state. Some tools have been developed to assess the information recorded by a physician (for example, "Systems And Methods For Determining Insufficient Medical Documentation"/U.S. Patent Application Publication No. 2016/0012187, "Physician And Clinical Documentation Specialist Workflow Integration"/U.S. Patent Application Publication No. 2013/0297347, or "Real-Time Synchronous Semantic Processing In Electronic Documentation"/U.S. Patent Application Publication No. 20110301966A1); but these tools seek to transform entered information into a structured form (such as a table that contains diagnosis codes and dates associated with the codes) and do not assist a physician to completely and clearly document and assess a particular medical condition based on the particular needs of that condition. There is, therefore, a need for a tool that analyzes a clinical narrative note for sufficiency of information to determine a patient's health status (e.g., whether the patient's heart's failure is compensated or decompensated) and provide feedback that is tailored to the needs and requirements of assessing that health status. The present disclosure is directed towards addressing this and other shortcomings of the prior art.

SUMMARY

In some embodiments, a computer-implemented method for documenting a patient's health status is disclosed. The data processing system includes a processing device and a memory comprising instructions which are executed by the processor to perform the method. The method includes receiving a classifier based on a machine learning algorithm trained on a database of clinical narrative notes, receiving a clinical narrative note from an end-user device through a notation assistant interface, processing the clinical narrative note to extract information related to the health of a patient, scoring the clinical narrative note using the classifier to produce a factor rating, and providing the rating to the end-user device for displaying to a user through the notation assistant interface.

In other embodiments, a notation assistant system is disclosed. The notation assistant system includes a machine learning system, a notation processing system, a scoring system, and a suggestion system. The machine learning system is configured to train a classification model based on a database of clinical narrative notes. The notation processing system is configured to perform natural language processing of a clinical narrative note input into a notation assistant interface to extract information. The scoring system is configured to input the extracted information into the classification model to produce at least one factor rating related to the clinical narrative note. The suggestion system is configured to generate a suggestion for modifying the clinical narrative note to improve the at least one factor rating.

In still other embodiments, a computer-implemented method for real-time feedback on a clinical narrative note through a data processing system is disclosed. The data processing system includes a processing device and a memory comprising instructions which are executed by the processor to perform the method. The method includes receiving textual data of a clinical narrative note from an end-user device through a notation assistant interface, as it is being entered by a user, processing the clinical narrative note to extract information related to the health of a patient, scoring the clinical narrative note using a classifier to produce a factor rating, and providing the factor rating to the end-user device for displaying to a user through the notation assistant interface. The method also includes receiving additional textual data as the user continues to enter the clinical narrative note, repeating the processing and scoring steps on said data, and updating the notation assistant interface to display an updated factor rating based on the updated clinical narrative note.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures:

FIG. 6 is an example user interface enabling a user to enter a clinical narrative note, according to an embodiment;

FIG. 7 is another example user interface providing a user with a suggestion for improving a completion score of the clinical narrative note, according to an embodiment; and FIG. 8 is another example user interface providing a user with a suggestion for improving a clarity score of the clinical narrative note, according to an embodiment.

DETAILED DESCRIPTION OF EXEMPLARY EMBODIMENTS

Figure 1:
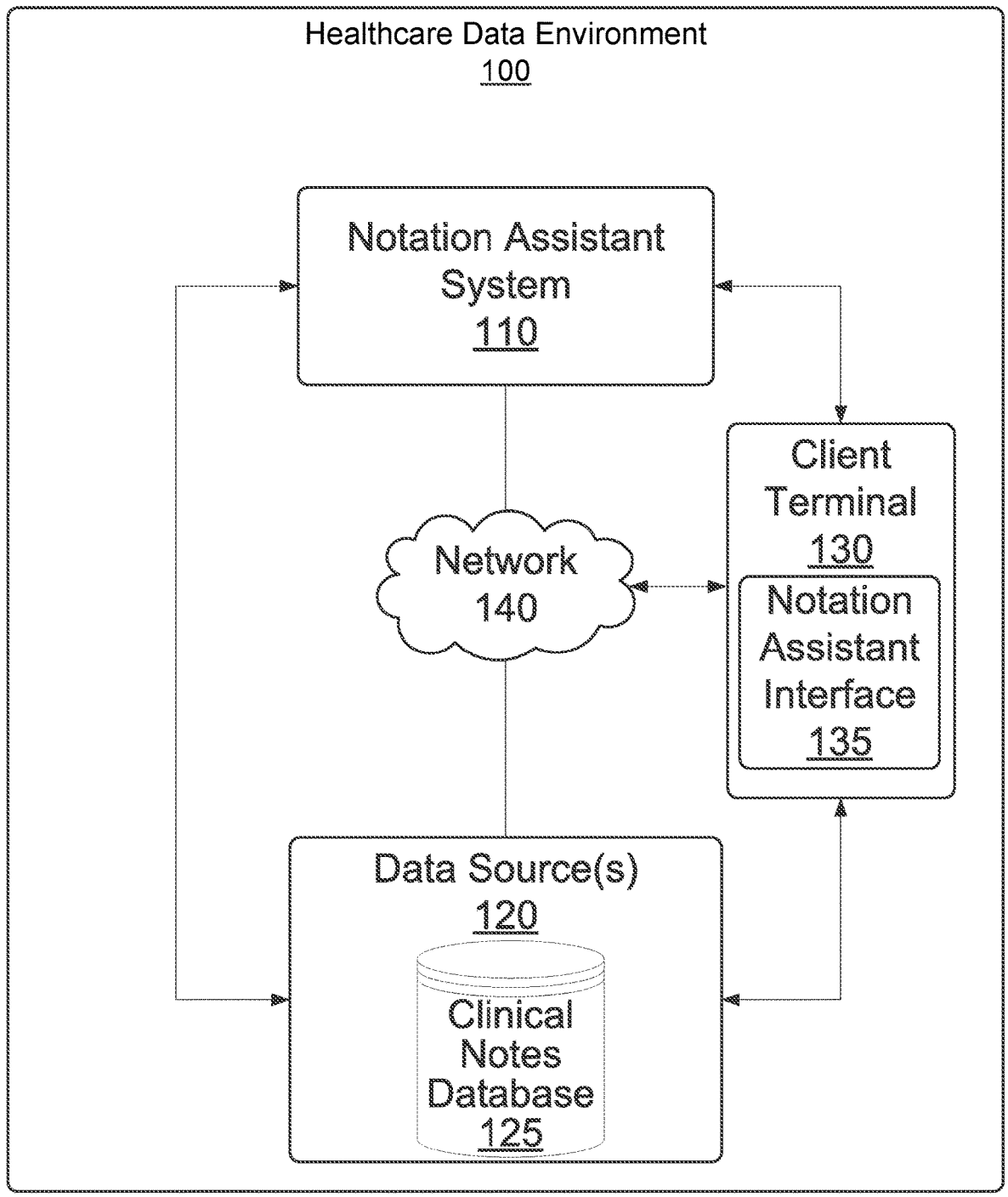
FIG. 1 is a block diagram of an example healthcare data environment, according to an embodiment.

Embodiments of the present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a head disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network (LAN), a wide area network (WAN) and/or a wireless network. The network may comprise copper transmission cables, optical transmission fibers, wireless transmission, routers, firewalls, switches, gateway computers, and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object-oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer, or entirely on the remote computer or server. In the latter scenario, the remote computer may be connected to the user's computer through any type of network, including LAN or WAN, or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operations steps to be performed on the computer, other programmable apparatus, or other device to produce a computer implemented process, such that the instructions which execute on the computer, other programmable apparatus, or other device implement the functions/acts specified in the flowcharts and/or block diagram block or blocks.

The flowcharts and block diagrams in the Figures illustrate the architecture, functionality, and operation of possible implementations of systems, methods, and computer program products according to various embodiments of the present invention. In this regard, each block in the flowcharts or block diagrams may represent a module, segment, or portion of instructions, which comprises one or more executable instructions for implementing the specified logical functions. In some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustrations, and combinations of blocks in the block diagrams and/or flowchart illustrations, can be implemented by special purpose hardware-based systems that perform the specified functions or acts or carry out combinations of special purpose hardware and computer instructions.

The present disclosure relates to a clinical notation assistant for analyzing clinical narrative notes from a physician and providing a real-time assessment of one or more factors, such as completion and clarity. The notation assistant may include a machine learning system configured to review example narrative notes from a database to train a classifier for assessing the one or more factors. The notation assistant may provide a score for the one or more factors and output the score to a user through an interface as the user is typing the clinical narrative note. The notation assistant may also provide suggestions for improving the clinical narrative note or prompt the user to answer questions to fill in missing or ambiguous information.

In some embodiments, the clinical notation assistant includes a classifier that is trained to review clinical narrative notes for completion and clarity with respect to a description of a health status of a patient having CHF. The classifier is trained to analyze the words and phrases entered by a user (e.g., a physician or other clinical user) and determine the degree to which the narrative completely and clearly describes the health status of the patient (e.g., whether the patient's heart is compensated or decompensated).

The notation assistant may be displayed to a user through a notation assistant interface (e.g., as part of an end-user device). The notation assistant interface may include an area for a user to enter narrative notes related to an evaluation of a patient. The notation assistant interface may relay the notes to a notation assistant system such that the notation assistant system may score one or more factors related to the notes in real-time. The notation assistant system may also produce one or more suggestions for the user to modify or improve the narrative notes while the user is entering the notes via the notation assistant interface, such as to improve a factor score (e.g., a completion score or a clarity score).

FIG. 1 is an illustration of an exemplary healthcare data environment 100. The healthcare data environment 100 may include a notation assistant system 110, one or more data sources 120 having a clinical notes database 125, and a client terminal 130 having a notation assistant interface 135. A network 140 may connect the notation assistant system 110, the one or more data sources 120, and/or the client terminal 130.

The notation assistant system 110 may be a computing device. The notation assistant system 110 may include components that enable disclosed functions for analyzing a clinical narrative note and providing feedback.

The one or more data sources 120 may be computing devices and/or storage devices configured to supply data to the notation assistant system 110 and/or the client terminal 130. For example, the one or more data sources 120 may include a clinical notes database 125 storing clinical narrative notes associated with medical records of a plurality of patients. The clinical notes database 125 may include patient medical details (such as labs, procedures, comorbidities). Additionally, the clinical notes database 125 may also include progress reports, office visit summaries, prescription order details, discharge summaries, among other types of documentation associated with the patients. The clinical notes database 125 may include clinical narrative notes, including any narrative content or notes entered by a user with regard to a patient's health. The clinical notes database 125 may particularly include clinical narrative notes associated with CHF patients. The clinical notes database 125 may additionally or alternatively store information associated with a compensated or decompensated status of a CHF patient's heart's failure.

The client terminal 130 may be an end-user computing device (e.g., a desktop or laptop computer, mobile device, etc.). The client terminal 130 may communicate with the notation assistant system 110 in order to receive and produce a notation assistant that is presented to a user through the notation assistant interface.

The network 140 may be a local or global network and may include wired and/or wireless components and functionality which enable internal and/or external communication for components of the healthcare data environment. The network 140 may be embodied by the Internet, provided at least in part via cloud services, and/or may include one or more communication devices or systems which enable data transfer to and from the systems and components of the healthcare data environment 100.

In accordance with some exemplary embodiments, the notation assistant system 110, data source(s) 120, client terminal 130, or the related components include logic implemented in specialized hardware, software executed on hardware, or any combination of specialized hardware and software executed on hardware, for implementing the healthcare data environment 100 or related components. In some exemplary embodiments, the notation assistant system 110 or any of its components may be or include the IBM Watson™ system available from International Business Machines Corporation of Armonk, N.Y., which is augmented with the mechanisms of the illustrative embodiments described hereafter.

Figure 2:
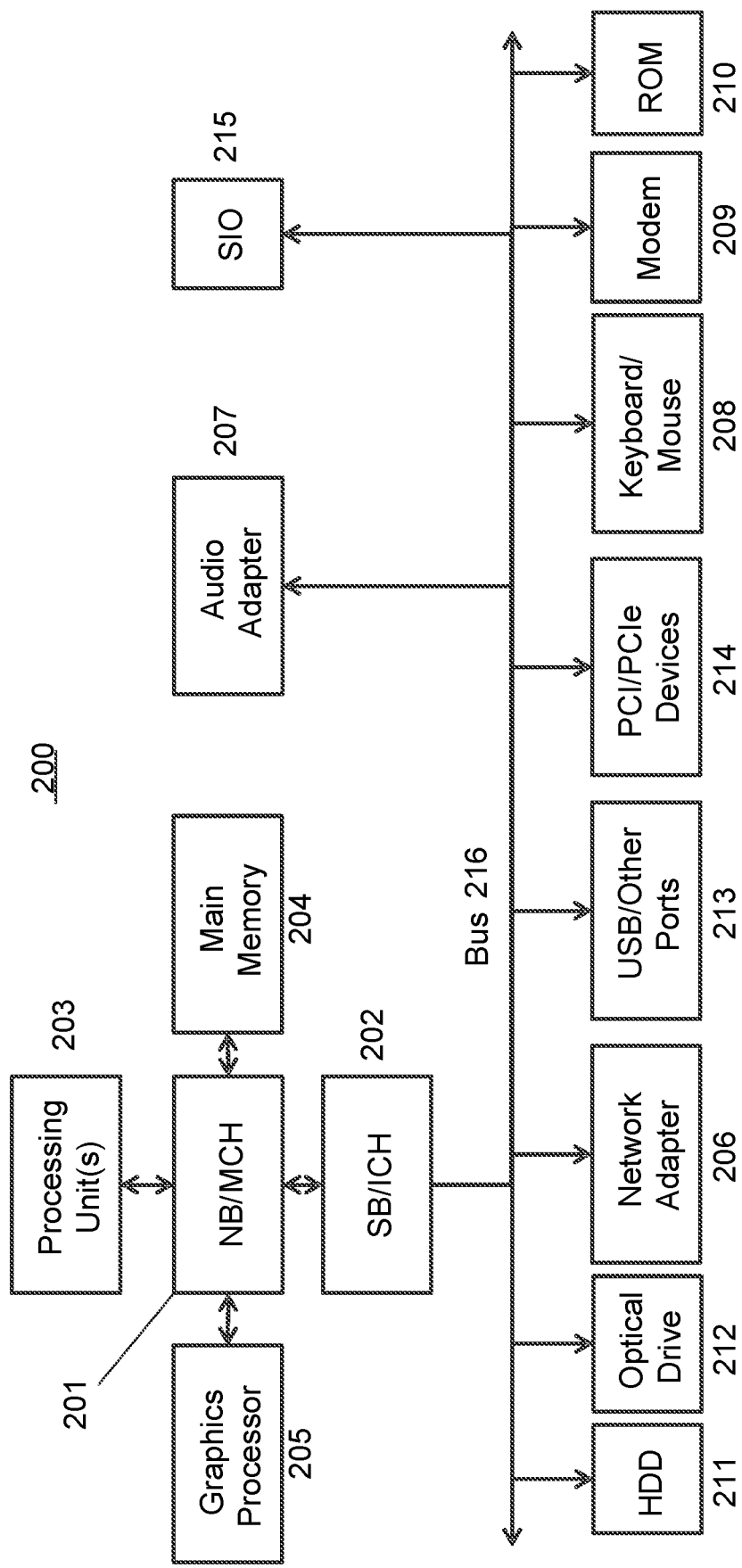
FIG. 2 is a block diagram of an example data processing system in which aspects of the illustrative embodiments are implemented.

FIG. 2 is a block diagram of an example data processing system 200 in which aspects of the illustrative embodiments may be implemented. Data processing system 200 is an example of a computer in which computer usable code or instructions implementing the process for illustrative embodiments of the present invention are located. In one embodiment, the data processing system 200 represents one or more of the notation assistant system 110, the one or more data sources 120, or the client terminal 130, and implements at least some of the functional aspects described herein.

In the depicted example, data processing system 200 can employ a hub architecture including a north bridge and memory controller hub (NB/MCH) 201 and south bridge and input/output (I/O) controller hub (SB/ICH) 202. Processing unit 203, main memory 204, and graphics processor 205 can be connected to the NB/MCH 201. Graphics processor 205 can be connected to the NB/MCH 201 through an accelerated graphics port (AGP).

In the depicted example, the network adapter 206 connects to the SB/ICH 202. The audio adapter 207, keyboard and mouse adapter 208, modem 209, read only memory (ROM) 210, hard disk drive (HDD) 211, optical drive (CD or DVD) 212, universal serial bus (USB) ports and other communication ports 213, and the PCI/PCIe devices 214 can connect to the SB/ICH 202 through bus system 216. PCI/PCIe devices 214 may include Ethernet adapters, add-in cards, and PC cards for notebook computers. ROM 210 may be, for example, a flash basic input/output system (BIOS). The HDD 211 and optical drive 212 can use an integrated drive electronics (IDE) or serial advanced technology attachment (SATA) interface. The super I/O (SIO) device 215 can be connected to the SB/ICH 202.

An operating system can run on processing unit 203. The operating system can coordinate and provide control of various components within the data processing system 200. As a client, the operating system can be a commercially available operating system. An object-oriented programming system, such as the Java™ programming system, may run in conjunction with the operating system and provide calls to the operating system from the object-oriented programs or applications executing on the data processing system 200. As a server, the data processing system 200 can be an IBM® eServer™ System p® running the Advanced Interactive Executive operating system or the Linux operating system. The data processing system 200 can be a symmetric multiprocessor (SMP) system that can include a plurality of processors in the processing unit 203. Alternatively, a single processor system may be employed.

Instructions for the operating system, the object-oriented programming system, and applications or programs are located on storage devices, such as the HDD 211, and are loaded into the main memory 204 for execution by the processing unit 203. The processes for embodiments of the website navigation system can be performed by the processing unit 203 using computer usable program code, which can be located in a memory such as, for example, main memory 204, ROM 210, or in one or more peripheral devices.

A bus system 216 can be comprised of one or more busses. The bus system 216 can be implemented using any type of communication fabric or architecture that can provide for a transfer of data between different components or devices attached to the fabric or architecture. A communication unit such as the modem 209 or network adapter 206 can include one or more devices that can be used to transmit and receive data.

Those of ordinary skill in the art will appreciate that the hardware depicted in FIG. 2 may vary depending on the implementation. For example, the data processing system 200 includes several components which would not be directly included in some embodiments of the notation assist system 110, data source(s) 120, or client terminal 130.

Moreover, other internal hardware or peripheral devices, such as flash memory, equivalent non-volatile memory, or optical disk drives may be used in addition to or in place of the hardware depicted. Moreover, the data processing system 200 can take the form of any of a number of different data processing systems, including but not limited to, client computing devices, server computing devices, tablet computers, laptop computers, telephone or other communication devices, personal digital assistants, and the like. Essentially, data processing system 200 can be any known or later developed data processing system without architectural limitation.

Figure 3:
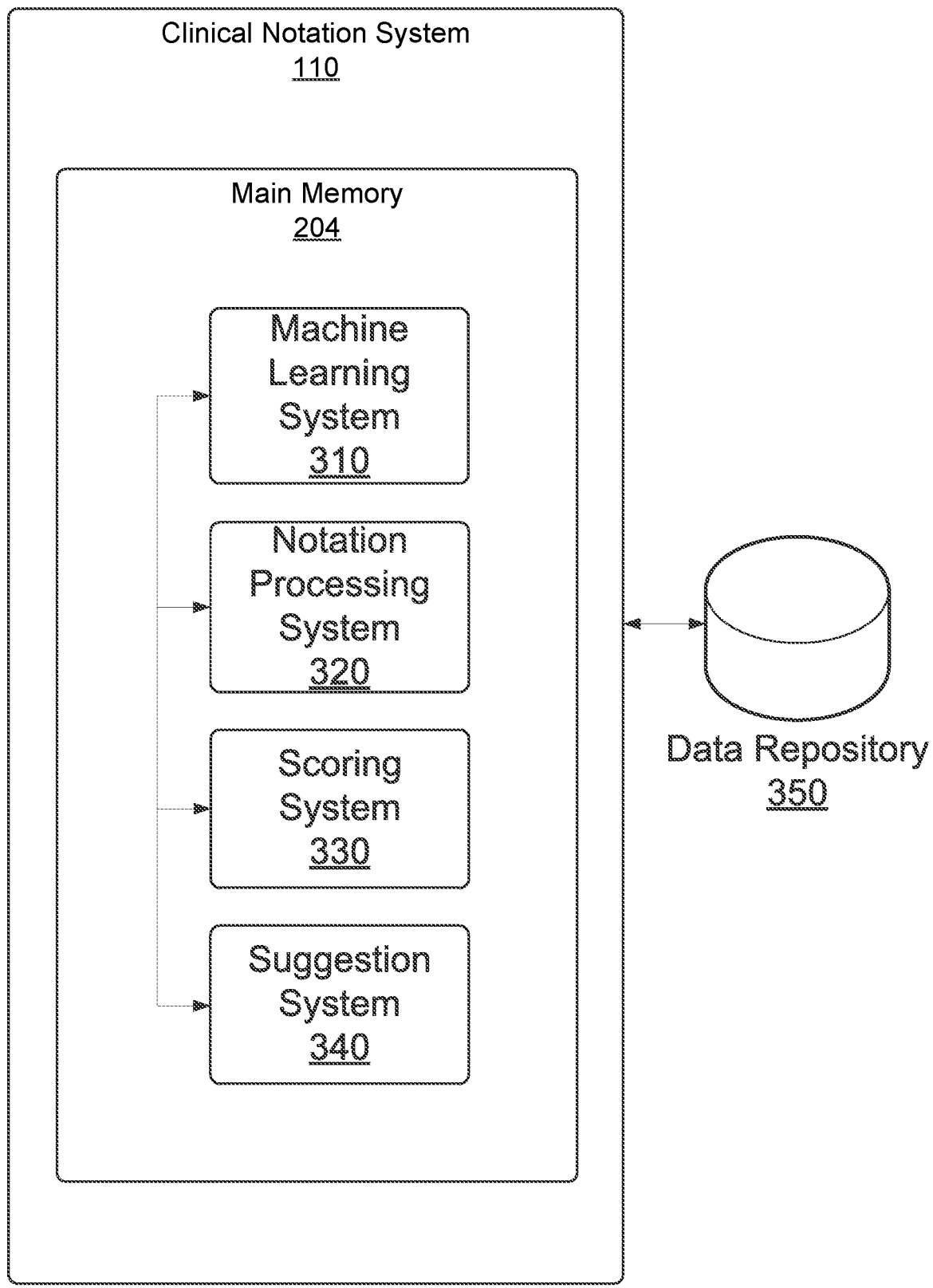
FIG. 3 is a block diagram of an example notation assistant system, according to an embodiment.

FIG. 3 illustrates an exemplary embodiment of the notation assistant system 110. In an exemplary embodiment, the notation assistant system 110 includes a machine learning system 310, a notation processing system 320, a scoring system 330, and a suggestion system 340. These subsystems of the notation assistant system 110 may be components of a single device, or may be separated devices connected to each other (e.g., via the network 140). In some embodiments, the notation assistant system 110 may further include and/or be connected to a data repository 350.

The machine learning system 310 may be a computing device or component (e.g., software or hardware engine or module) configured to generate a classifier using a machine learning process. The machine learning system 310 is configured to use information in the one or more data sources 120 to train a classifier to assess one or more factors associated with clinical narrative notes. For example, the machine learning system 310 may review clinical narrative notes (and optionally with additional structured variables such as laboratory measurements, comorbidities, medications, etc.) from the database 125 and use supervised or unsupervised learning to develop classifiers for scoring narrative notes. In an exemplary embodiment, the machine learning system 310 is configured to develop a completion classifier and a clarity classifier. In some embodiments, the machine learning system 310 may generate a classification model that produces multiple factor ratings based on input information extracted from a clinical narrative note.

In some embodiments, the machine learning system 310 is configured to develop machine learning algorithms (often referred as "artificial intelligence" with additional titles such as "deep learning", "supervised learning", "unsupervised learning", etc.) trained on clinical narrative notes from the database 125 that describe the condition of a CHF patient. For example, the machine learning system 310 may use a deep learning algorithm based on clinical narrative notes for CHF patients and known compensated or decompensated status of these patients to identify the information that is needed to assess a CHF patient's heart's health status. In another embodiments each note may be labeled by additional labels beyond "compensated" or "decompensated." For example, notes may be classified as "compensated: implicit", "compensated: explicit", "decompensated: implicit", "decompensated: explicit", or as "heart failure status: indeterminate." The machine learning algorithm used will be able to provide a classification to one of the multiclass possibilities for a given note.

In some embodiments, the machine learning system 310 may additionally or alternatively generate an algorithm or a classifier to categorize a health status of a patient based on a clinical narrative note. For instance, the machine learning system 310 may be configured to generate a machine learning algorithm configured to classify a heart health status of a patient based on a clinical narrative note (e.g., compensated or decompensated). The machine learning system 310 may be configured to assess multiple conditions of a patient at a time of a visit (e.g., heart health, viral or bacterial diagnosis, pneumonia status, etc.).

The notation processing system 320 may be a computing device or component (e.g., software or hardware engine or module) configured to receive and process narrative notes from the client terminal 130 (e.g., via the notation assistant interface 135). In one example, a user may enter notes via the notation assistant interface 135 and the notation processing system 320 may use natural language processing to extract information from the narrative notes. For example, the notation processing system 320 may extract objective information that is related to the patient's health. In one embodiment, the notation processing system 320 extracts terms that indicate symptoms (e.g., pain, fever, etc.), background (e.g., age, gender, ethnicity, etc.), appearance (pale, distressed, etc.), or physiological observations (e.g., blood pressure, heart rate, etc.). In another example, the notation processing system 320 may extract subjective information related to the physician's judgement or choice of words, such as adjectives, declarations, terms indicating opinion or fact, confidence levels, etc.

The scoring system 330 may be a computing device or component (e.g., software or hardware engine or module) configured to analyze the information extracted by the notation processing system 320 and provide a factor rating based on a classifier developed by the machine learning system 310 related to a selected factor. In one example, the scoring system 330 is configured to establish a completion score and a clarity score. However, it should be understood that the scoring system 330 may provide a factor rating according to one or more other factors. In an exemplary embodiment, the scoring system 330 is configured to determine a completion score that is a rating of how complete a notation is with respect to information needed to assess the health status of a patient's heart (e.g., compensated or decompensated). The completion score may thus be an assessment of how much information is provided in the notation. Similarly, the scoring system 330 is configured to determine a clarity score that is a rating of how easily one may be able to determine a health status from the narrative notes. The clarity score may thus be an assessment of whether the notation is ambiguous. The scoring system 330 may use the objective and subjective information extracted from the clinical narrative note to determine the completion and clarity scores based on the classifiers.

The suggestion system 340 may be a computing device or component (e.g., software or hardware engine or module) configured to provide feedback to a user based on a clinical narrative note. The suggestion system 340 is configured to consider information that is part of a clinical narrative note (e.g., the objective and subjective information extracted by the notation processing system 320), determine what is missing or unclear, and provide suggestions for what information could be entered to improve the note. In one example, the suggestion system 340 may use a checklist system to inform a user of the information that is missing from a clinical narrative note and that would increase a completion score. In another example, the suggestion system 340 may identify terms or phrases that are unclear and suggest that they be revised to improve clarity of the notation.

The data repository 350 may be a database configured to store data. The data repository 350 may be configured to receive data from the notation assistant system 110 and/or from one or more data sources 120 and store the data according to appropriate storage protocols. In some embodiments, the data repository 350 receives data from the notation assistant system 110, such as from the notation processing system 320 in order to improve the dataset usable by the machine learning system 310 for developing a classifier. In other embodiments, the data repository 350 receives data from the one or more data sources 120 and is a data supply for the notation assistant system 110.

Figure 4:
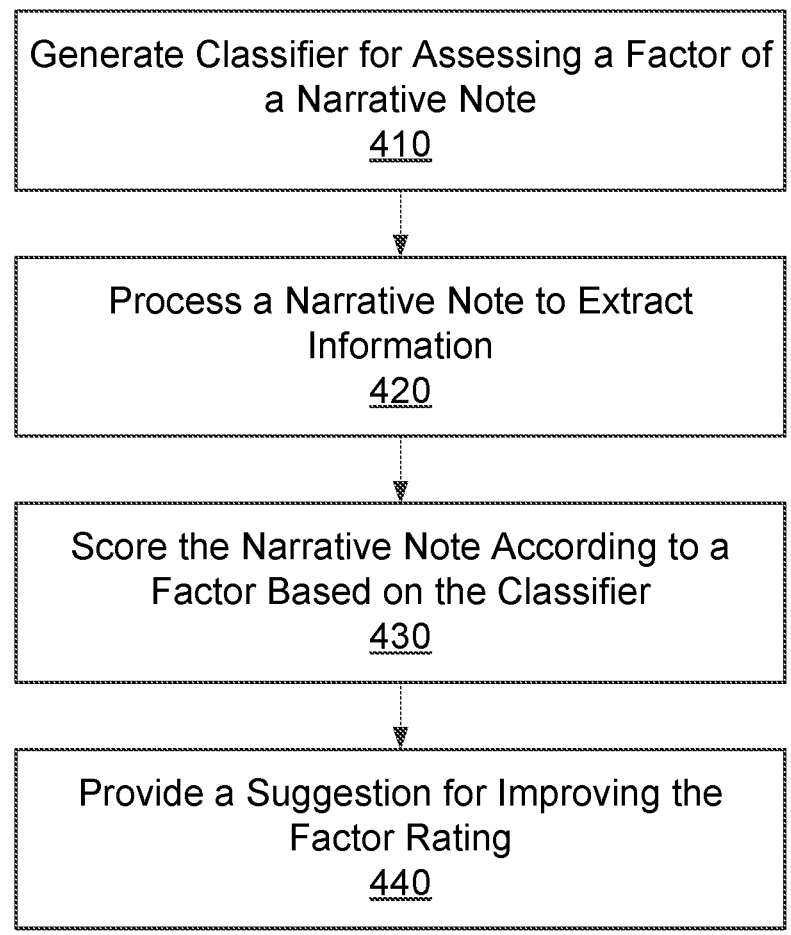
FIG. 4 is a flowchart of an example data notation assistant process, according to an embodiment.

FIG. 4 is a flowchart of an exemplary notation assistant process 400. The notation assistant system 110 may perform one or more steps of the process 400 in order to provide analysis of a clinical narrative note. In an exemplary embodiment, the process 400 may provide feedback to a user entering a clinical narrative note related to the health status of a CHF patient.

In step 410, the machine learning system 310 trains a classifier for assessing at least one factor of a clinical narrative note. For example, the machine learning system 310 may review examples of clinical narrative notes in the database 125 and use machine learning to develop a classifier for assessing the completion and/or clarity of a narrative note, with respect to narrative notes with known factor scores. For example, the machine learning system 310 may train a completion classifier based on known complete and incomplete narrative notes. In another example, the machine learning system 310 may train an ambiguity classifier based on known clear and unclear narrative notes. In this way, the machine learning system 310 may train a classifier for determining a factor rating related to a health status of a CHF patient. For instance, a completion classifier may be configured to determine how completely a narrative note describes information needed to assess a compensated or decompensated status of a patient's heart. Similarly, an ambiguity classifier may be configured to determine how clearly the narrative note describes the information need to assess the heart health status.

In step 420, the notation processing system 320 processes a narrative note. In one example, a user enters a narrative note into the client terminal 130 via the notation assistant interface 135, and the client terminal sends the information to the notation assistant system 110. The notation processing system 320 performs, for example, natural language processing of the received narrative note to extract relevant information from the narrative note. In one embodiment, the notation processing system 320 extracts both objective and subjective information from the clinical narrative note.

In step 430, the scoring system 330 determines a factor rating for one or more factors related to the received narrative note based on the extracted information. In one example, the scoring system 330 determines a completion score that rates a degree to which the narrative note is complete in identifying the information needed to assess a health status of the patient. In another example, the scoring system determines a clarity score that rates a degree to which the narrative note is clear with respect to the information needed to assess the health status of the patient. The scoring system 330 determines the factor rating and provides the rating to the client terminal 130 for displaying to the user through the notation assistant interface 135.

In some embodiments, the scoring system 330 may also determine whether the information in the clinical narrative note is sufficient to determine a health status. For instance the scoring system 330 may determine whether the information in the clinical narrative note is sufficient to determine whether the CHF patient's heart is compensated or decompensated. The notation assistant system 110 may provide the health status to the notation assistant interface 135. In some instances, if the health status is indeterminate (e.g., because the completion and clarity scores are low) the scoring system 330 may provide the indeterminate status to the notation assistant interface 135.

In step 440, the suggestion system 340 determines a suggestion for providing to the user for modifying the clinical narrative note to improve one or more of the factor ratings. In one example, the suggestion system 340 may provide a suggestion for improving a completion score and/or a clarity score of the clinical narrative note. The suggestion system 340 may provide suggestions for missing information, improving unclear statements, resolving discrepancies, or correcting likely errors. In one example, the suggestion system 340 may provide suggested words for adding to or replacing part of a clinical narrative note.

The notation assistant process 400 is an example of a process that may be used for providing a suggestion to improve a clinical narrative note with respect to a CHF patient and a documenting of a compensated or decompensated status of the patient's heart. The notation assistant system 110 may perform one or more steps of the process 400 to assist a user in entering a complete and clear notation that improves the likelihood that the note can be used to accurately assess the health status of the patient's heart at the time the notation is written. The notation assistant system 110 may perform process 400 to score a complete clinical narrative note, provide the factor rating, and, in some instances, provide suggestions for improving the factor rating. The notation assistant system 110 may process clinical narrative notes to assess quality of data for patients who received care in the past, such as to allow a comparison of factor ratings of completed notes between different physicians, institutions, etc. In some embodiments, the process 400 may include the notation assistant system 110 providing a real-time analysis and scoring of a clinical narrative note while the physician (or other user) is entering the note via the notation assistant interface 135.

Figure 5:
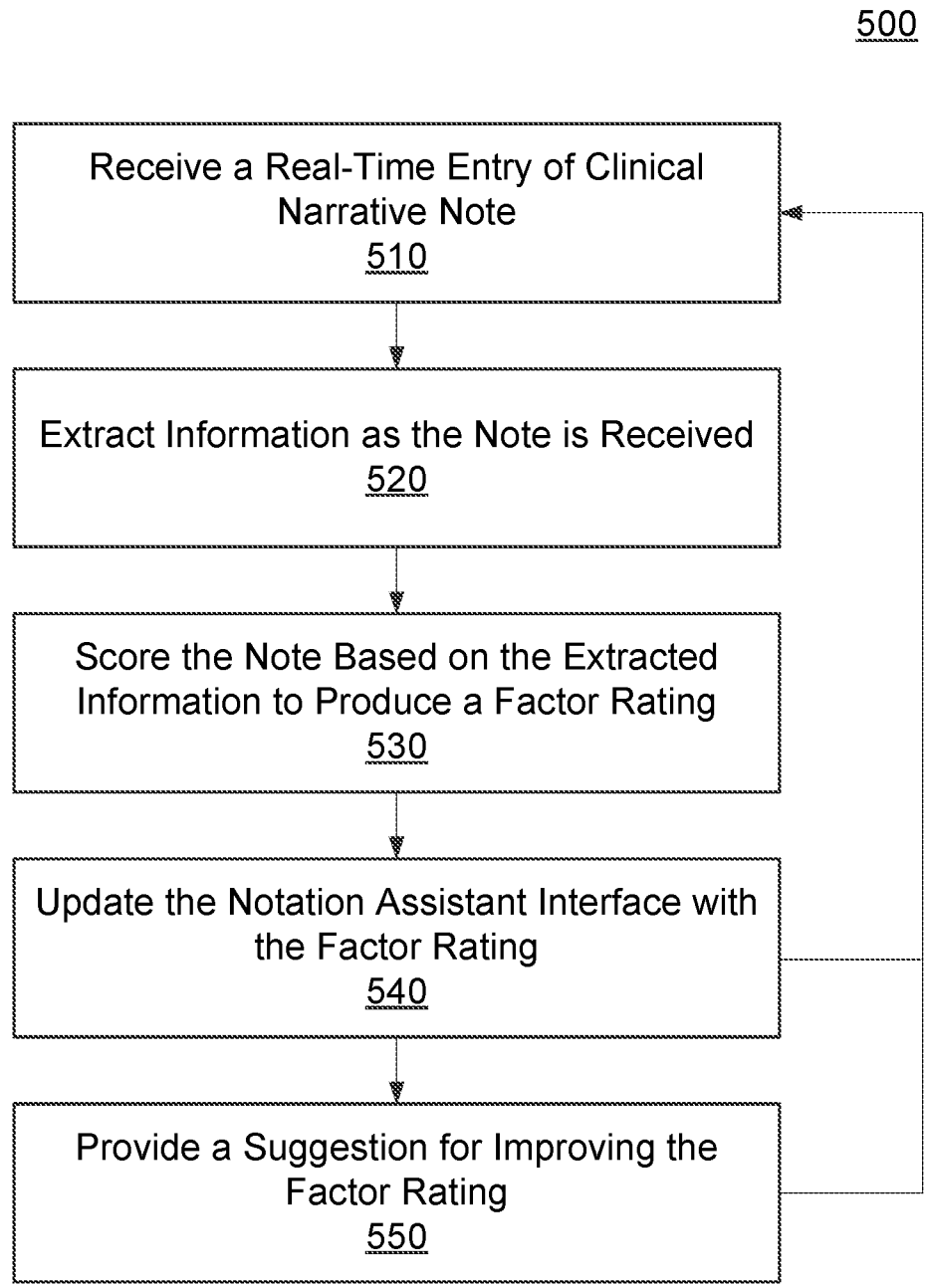
FIG. 5 is a flowchart of an example real-time feedback process, according to an embodiment.

FIG. 5 is a flowchart of an exemplary process 500 for providing real-time feedback of a clinical narrative note as a user enters the note via the notation assistant interface 135. The notation assistant system 110 may perform one or more steps of the process 500. In some embodiments, the process 500 may overlap with the process 400. For example, the process 500 may use one or more factor classifiers generated in step 410 of process 400. For instance, the process 500 may use a completion classifier and an ambiguity classifier trained on clinical narrative notes by the machine learning system 310.

In step 510, the notation assistant system 110 receives a real-time entry of a clinical narrative note. For instance, the notation processing system 320 may receive continuous or periodic updates of textual information entered into a note field of the notation assistant interface 135. In some embodiments, the notation assistant interface 135 may include a selectable analysis trigger (e.g., a "submit" or "analyze" button) that causes the entered information to be sent to the notation assistant system 110. In one embodiment, the client terminal 130 may send in-progress note information to the notation assistant system 110 via the network 140. In another embodiment, the notation assistant system 110 and client terminal 130 may be one integrated device or series of directly connected devices.

In step 520, the notation assistant system 110 extracts information from the received clinical narrative note. For example, the notation processing system 320 may analyze the words and phrases that have been received, as they are received. In another example, the notation processing system 320 may process the received information after a threshold has been reached (e.g., a full sentence, a number or words, an analysis trigger has been selected by the user and received, etc.). The notation assistant system 110 may extract objective and subject information and provide the extracted information to the scoring system 330.

In step 530, the notation assistant system 110 determines a factor rating for the note based on the extracted information. For instance, the scoring system 330 may use a factor classifier to analyze the extracted information and determine a factor rating associated with the classifier based on the note as it stands. In some embodiments, the factor rating may be a numerical score (e.g., a percentage from 0-100, a rating on a scale of 0-1, etc.). The scoring system 330 may be configured to provide a completion score and a clarity score based on a completion classifier and an ambiguity classifier, respectively.

In step 540, the notation assistant system 110 updates the notation assistant interface 135 with the factor rating. For example, the scoring system 330 may provide the numeral score to the client terminal 130 for displaying via the notation assistant interface 135. In some embodiments, the scoring system 330 may provide a plurality of factor ratings for a single clinical narrative note. For instance, the scoring system 330 may provide a completion score and a clarity score to the client terminal 130.

In some embodiments, the notation assistant system 110 may continuously update the factor rating in real-time as the user inputs the clinical narrative note. For instance, the steps 510-540 may repeat at certain intervals, thresholds, or user trigger points. The notation assistant system 110 may also continuously determine whether the information is sufficient to characterize a health status of the patient and may provide the status to the notation assistant interface 135. For instance, the scoring system 330 may use a machine learning algorithm from the machine learning system 310 to characterize a clinical narrative note as indicating a health condition. The scoring system 330 may set the health condition as indeterminate and adjust the determination as more information is extracted from textual data input by the user.

In step 550, the notation assistant system 110 provides a suggestion for improving the factor rating. For example, the suggestion system 340 may track missing information and provide suggestive feedback to the notation assistant interface as the user is entering the note. In another example, the suggestion system 340 may highlight entered text and provide specific feedback (e.g., suggestions) for modifying the text (e.g., with specific examples).

The process 500 enables the notation assistant interface 135 to receive textual information and provide real-time feedback that assists the user in entering information that will lead to an effective recording of a patient's health status and visit with the physician (or other clinical user). In an exemplary embodiment, the notation assistant interface 135 provides continuous feedback in the form of an updatable factor rating, such as a completion score and/or a clarity score based on the information that has been entered.

FIG. 6 is an example of a user interface 600. The user interface 600 may be an example of a notation assistant interface 135. The user interface 600 may be displayed to a user and have interactive features enabling the user to provide information through one or more I/O devices (e.g., keyboard, mouse, touchscreen, etc.). The user interface 600 may include a field for a user to type a clinical narrative note 605. The clinical narrative note 605 is a freely written narrative of an assessment of a patient.

In an exemplary embodiment, the client terminal 130 may send the narrative note 605 to the notation assistant system 110. The notation assistant system 110 may process the narrative note 605 to extract information (e.g., variables) from the textual content of the note 605. In some instances, the notation assistant system 110 may perform natural language processing to extract information. In one embodiment, the notation assistant system 110 may identify and/or extract objective medical information 610 and subjective input 620 within the narrative note. In the example of user interface 600, the user has entered several words and phrases that indicate symptoms, conditions, and background information of the patient (examples of objective medical information 610). Moreover, the user has entered phrases that indicate the subjective judgment of the user (examples of subjective input 620).

The notation assistant system 110 is configured to input the extracted information 610, 620 into a classification model to determine one or more factor ratings that characterize the narrative note 605. For example, the notation assistant system 605 is configured to provide a completion score 630 and a clarity score 640.

FIGS. 7 and 8 are examples of user interfaces 700, 800 respectively that provide suggestions to the user for improving a score of a narrative note. The user interface 700 provides a suggestion for improving a completion score. For instance, the user interface 700 provides a checklist 710 that includes possible information that could be added to the narrative note to provide more information that would satisfy criteria for the completion score. The user interface 800 provides a suggestion for improving a clarity score. For instance, the user interface 800 highlights a phrase 805 that may be ambiguous and provides several options in a suggestion field 810 for the user to replace the ambiguous phrase 805 in a manner that would make the narrative more clear. For instance, instead of saying "some degree of congestive heart failure" the use may select that "the heart is decompensated."

The disclosed notation assistant system is applicable to documentation systems, such as medical charting or recording software for receiving and retaining medical information. The notation assistant system may be integrated with software used by medical institutions to input and retain patient data. The notation assistant system may provide feedback that is specifically tailored to a particular medical condition, such as the health status of a CHF patient's heart. It should be understood, however, that the disclosed embodiments are not limited to CHF patients and heart health, and could be used to improve clinical narrative notes related to many different health conditions.

The disclosed embodiments provide several advantages, including allowing a user to see how well they have documented certain information, as well as to receive suggestions for modifying their input. The disclosed embodiments are specifically tailored to characteristic factors, such as completion and clarity that are relevant to understanding whether a narrative note is sufficient to establish a patient's health status to a high confidence level.

The present description and claims may make use of the terms "a," "at least one of," and "one or more of," with regard to particular features and elements of the illustrative embodiments. It should be appreciated that these terms and phrases are intended to state that there is at least one of the particular features or elements present in the particular illustrative embodiment, but that more than one can also be present. That is, these terms/phrases are not intended to limit the description or claims to a single feature/element being present or require that a plurality of such features/elements be present. On the contrary, these terms/phrases only require at least a single feature/element with the possibility of a plurality of such features/elements being within the scope of the description and claims.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples are intended to be non-limiting and are not exhaustive of the various possibilities for implementing the mechanisms of the illustrative embodiments. It will be apparent to those of ordinary skill in the art in view of the present description, that there are many other alternative implementations for these various elements that may be utilized in addition to, or in replacement of, the example provided herein without departing from the spirit and scope of the present invention.

The system and processes of the Figures are not exclusive. Other systems, processes and menus may be derived in accordance with the principles of embodiments described herein to accomplish the same objectives. It is to be understood that the embodiments and variations shown and described herein are for illustration purposes only. Modifications to the current design may be implemented by those skilled in the art, without departing from the scope of the embodiments. As described herein, the various systems, subsystems, agents, managers, and processes can be implemented using hardware components, software components, and/or combinations thereof. No claim element herein is to be construed under the provisions of 35 U.S.C. 112, sixth paragraph, unless the element is expressly recited using the phrase "means for."

Although the invention has been described with reference to exemplary embodiments, it is not limited thereto. Those skilled in the art will appreciate that numerous changes and modifications may be made to the preferred embodiments of the invention and that such changes and modifications may be made without departing from the true spirit of the invention. It is therefore intended that the appended claims be construed to cover all such equivalent variations as fall within the true spirit and scope of the invention.

What is claimed is:

1. A computer-implemented method for assisting the assessing of a patient's health status, comprising a processing device and a memory comprising instructions which are executed by the processor, the method comprising:
   training an ambiguity classifier, based on a plurality of clear narrative notes and a plurality of unclear narrative notes, to assess a clarity of a received clinical narrative note;
   receiving the received clinical narrative note from an end-user device through a notation assistant interface, wherein the clinical narrative note comprises a sentence comprising a subjective judgement;
   processing the received clinical narrative note to extract information related to the health of a patient;
   scoring the received clinical narrative note using the ambiguity classifier to produce a clarity score;
   providing a clarity suggestion for modifying the received clinical narrative note to improve the clarity score to the end-user device, wherein providing the clarity suggestion comprises:
      identifying the sentence comprising a subjective judgement, and
      suggesting a replacement sentence to replace the sentence comprising the subjective judgement; and
   providing the clarity score and the clarity suggestion to the end-user device for displaying to a user through the notation assistant interface.

2. The method of claim 1, wherein processing the clinical narrative note comprises performing natural language processing on the clinical narrative note.

3. The method of claim 2, wherein the extracted information includes objective medical information.

4. The method of claim 1, wherein the method further comprises:
   training a completion classifier, based on a plurality of complete narrative notes and a plurality of incomplete narrative notes, to assess the completion of a received clinical narrative note;

scoring the received clinical narrative note using the completion classifier to produce a completion score; and providing the completion score to the end-user device for displaying to a user through the notation assistant interface.

5. The method of claim 4, wherein the completion score comprises a first numerical score.

6. The method of claim 1, wherein the clarity score comprises a second numerical score.

7. The method of claim 4, further comprising providing a completion suggestion for modifying the clinical narrative note to improve the completion score to the end-user device.

8. The method of claim 7, wherein the completion suggestion includes information that could be added to the clinical narrative note to improve the completion score.

9. A notation assistant system, comprising:
a machine learning system configured to train a clarity classification model to assess a clarity of a received clinical narrative note, wherein the clarity classification model is trained on a plurality of clear clinical narrative notes and a plurality of unclear narrative notes;
a notation processing system configured to perform natural language processing of the received clinical narrative note input into a notation assistant interface to extract information, wherein the received clinical narrative note comprises a sentence comprising a subjective judgement;
a scoring system configured to input the extracted information into the classification model to produce a clarity score; and
a suggestion system configured to generate a clarity suggestion for modifying the clinical narrative note to improve the clarity score by identifying the sentence comprising a subjective judgement, and suggesting a replacement sentence to replace the sentence comprising the subjective judgement.

10. The notation assistant system of claim 9, wherein the plurality of clear clinical narrative notes and the plurality of unclear narrative notes describe a health status of a patient's heart.

11. The notation assistant system of claim 9, wherein the machine learning system is further configured to train a classifier for determining a heart health status of the patient.

12. The notation assistant system of claim 11, wherein the heart health status of the patient is compensated, decompensated, or indeterminate.

13. The notation assistant system of claim 9, wherein the extracted information includes objective medical data.

14. The notation assistant system of claim 13, wherein the machine learning system is further configured to train a completion classifier to assess a completion of a received clinical narrative note, wherein the completion classifier is trained on a plurality of complete clinical narrative notes and a plurality of incomplete narrative notes, the scoring system is further configured to use the completion classifier to produce a completion score.

15. The notation assistant system of claim 14, wherein the suggestion system is further configured to generate a completion suggestion for modifying the clinical narrative note to improve the completion score.

16. A computer-implemented method for providing real-time feedback on a clinical narrative note, comprising a processing device and a memory comprising instructions which are executed by the processor, the method comprising:

training an ambiguity classifier, based on a plurality of clear narrative notes and a plurality of unclear narrative notes, to assess a clarity of textual data of a received clinical narrative note;
training a completion classifier, based on a plurality of complete narrative notes and a plurality of incomplete narrative notes, to assess the completion of a received clinical narrative note;
receiving the textual data of the received clinical narrative note from an end-user device through a notation assistant interface as it is being entered by a user, wherein the textual data of the received clinical narrative note comprises a sentence comprising a subjective judgement;
processing the received clinical narrative note to extract information related to the health of a patient;
scoring the received clinical narrative note using the ambiguity classifier to produce a clarity score;
scoring the received clinical narrative note using the completion classifier to produce a completion score; and
providing a clarity suggestion to the end-user device for displaying to the user through the notation assistant interface while the user is entering the clinical narrative note, wherein providing a clarity suggestion comprises:
identifying the sentence comprising a subjective judgement, and
suggesting a replacement sentence to replace the sentence comprising the subjective judgement; and
providing the clarity score, the clarity suggestion, and the completion score to the end-user device for displaying to a user through the notation assistant interface;
receiving more textual data as the user continues to enter the received clinical narrative note;
repeating the processing and scoring steps on the more textual data; and
updating the notation assistant interface to display an updated clarity score and an updated completion score based on the updated clinical narrative note.

17. The method of claim 1, further comprising:
providing a completion checklist, wherein the completion checklist comprises a list of information present in a complete clinical narrative note;
comparing the received clinical narrative note to the completion checklist;
identifying a missing information, wherein the missing information is an item on the checklist that is not in the received clinical narrative note; and
providing the missing information to the end-user device for displaying to a user through the notation assistant interface.

18. The method of claim 1, wherein the received clinical narrative note comprises a discrepancy, the method further comprising:
identifying the discrepancy in the received clinical narrative note; and
providing a discrepancy suggestion, wherein the discrepancy suggestion comprises a suggestion to resolve the discrepancy.

19. The method of claim 1, wherein the received clinical narrative note comprises a likely error, the method further comprising:
identifying the likely error in the received clinical narrative note; and providing a likely error suggestion, wherein the likely error suggestion comprises a suggestion to resolve the likely error.

\* \* \* \* \*